United States Patent
Shull et al.

[19]

[11] Patent Number: 6,143,022
[45] Date of Patent: Nov. 7, 2000

[54] STENT-GRAFT ASSEMBLY WITH DUAL CONFIGURATION GRAFT COMPONENT AND METHOD OF MANUFACTURE

[75] Inventors: Samuel L. Shull; John E. Nolting, both of Santa Rosa, Calif.

[73] Assignee: Medtronic AVE, Inc., Santa Rosa, Calif.

[21] Appl. No.: 09/139,285

[22] Filed: Aug. 24, 1998

[51] Int. Cl.[7] .................................................. A61F 2/06
[52] U.S. Cl. ..................... 623/1.13; 623/1.16; 623/1.18; 623/1.2
[58] Field of Search ..................... 606/108, 191, 606/194, 195, 198; 623/1, 11, 12, 1.12, 1.13, 1.15, 1.16, 1.18, 1.19, 1.2

[56] References Cited

U.S. PATENT DOCUMENTS

| | | | |
|---|---|---|---|
| 4,300,244 | 11/1981 | Bokros | 623/1 |
| 4,728,328 | 3/1988 | Hughes et al. | 623/1 |
| 4,731,073 | 3/1988 | Robinson | 623/1 |
| 4,776,337 | 10/1988 | Palmaz | 128/343 |
| 5,078,726 | 1/1992 | Kreamer | 606/194 |
| 5,123,917 | 6/1992 | Lee | 623/1 |
| 5,207,960 | 5/1993 | Moret de Rocheprise | 264/103 |
| 5,282,823 | 2/1994 | Schwartz et al. | 606/198 |
| 5,282,860 | 2/1994 | Matsuno et al. | 623/12 |
| 5,330,500 | 7/1994 | Song | 606/198 |
| 5,360,443 | 11/1994 | Barone et al. | 623/1 |

(List continued on next page.)

FOREIGN PATENT DOCUMENTS

| | | |
|---|---|---|
| 0 466 518 A2 | 1/1992 | European Pat. Off. . |
| 0 556 850 A1 | 8/1993 | European Pat. Off. . |
| 0 621 016 A1 | 10/1994 | European Pat. Off. . |
| 0 657 147 A3 | 6/1995 | European Pat. Off. . |
| 0 686 379 A2 | 12/1995 | European Pat. Off. . |
| 0 689 805 A3 | 3/1996 | European Pat. Off. . |
| 0 701 800 A1 | 3/1996 | European Pat. Off. . |
| 0 712 614 A1 | 5/1996 | European Pat. Off. . |
| 0 747 020 A3 | 11/1996 | European Pat. Off. . |
| 0 797 963 A2 | 1/1997 | European Pat. Off. . |
| 0 775 472 A2 | 5/1997 | European Pat. Off. . |
| 0 819 412 A2 | 1/1998 | European Pat. Off. . |
| WO 84/03036 | 8/1984 | WIPO . |
| WO 95/05132 | 2/1995 | WIPO . |
| WO 96/14808 | 5/1996 | WIPO . |
| WO 96/21404 | 7/1996 | WIPO . |
| WO 96/39104 | 12/1996 | WIPO . |

*Primary Examiner*—Vincent Millin
*Assistant Examiner*—Tram A. Nguyen

[57] ABSTRACT

A stent-graft assembly and method of preparing the same are disclosed. In a first embodiment, the assembly comprises a stent and a graft, wherein the graft has a delivery configuration and a treatment configuration in relation to the stent. In the delivery configuration, the graft material is longer than the stent, covers the outer diameter of the stent, and is folded under and into the inner diameter of the stent. In the treatment configuration, the graft is shorter in length than the stent, such that the graft is no longer folded under the ends and the end regions of the stent are uncovered. The graft is sufficiently affixed to the stent to prevent migration of the graft, yet sufficiently free of the stent such that it can assume a second configuration upon deployment of the device.

2 Claims, 6 Drawing Sheets

U.S. PATENT DOCUMENTS

| | | | |
|---|---|---|---|
| 5,389,106 | 2/1995 | Tower | 606/198 |
| 5,443,496 | 8/1995 | Schwartz | 623/1 |
| 5,449,382 | 9/1995 | Dayton | 623/1 |
| 5,489,295 | 2/1996 | Piplani | 623/1 |
| 5,507,771 | 4/1996 | Gianturco | 606/198 |
| 5,522,880 | 6/1996 | Barone et al. | 623/1 |
| 5,522,881 | 6/1996 | Lentz | 623/1 |
| 5,522,882 | 6/1996 | Gaterud et al. | 623/1 |
| 5,534,287 | 7/1996 | Lukic | 427/2.25 |
| 5,556,414 | 9/1996 | Turi | 606/198 |
| 5,562,728 | 10/1996 | Lazarus et al. | 623/1 |
| 5,571,173 | 11/1996 | Parodi | 623/1 |
| 5,578,071 | 11/1996 | Parodi | 623/1 |
| 5,578,072 | 11/1996 | Barone et al. | 623/1 |
| 5,591,195 | 1/1997 | Taheri et al. | 623/1 |
| 5,628,785 | 5/1997 | Schwartz et al. | 623/1 |
| 5,628,786 | 5/1997 | Banas et al. | 623/1 |
| 5,628,788 | 5/1997 | Pinchuk | 623/1 |
| 5,632,772 | 5/1997 | Alcime et al. | 623/1 |
| 5,637,113 | 6/1997 | Tartaglia et al. | 623/1 |
| 5,639,278 | 6/1997 | Dereume et al. | 623/1 |
| 5,641,373 | 6/1997 | Shannon et al. | 156/242 |
| 5,645,559 | 7/1997 | Hachtman et al. | 606/198 |
| 5,653,743 | 8/1997 | Martin | 623/1 |
| 5,653,747 | 8/1997 | Dereume | 623/1 |
| 5,667,523 | 9/1997 | Bynon | 606/198 |
| 5,674,241 | 10/1997 | Bley et al. | 606/198 |
| 5,674,276 | 10/1997 | Andersen et al. | 623/1 |
| 5,681,345 | 10/1997 | Euteneuer | 623/1 |
| 5,683,448 | 11/1997 | Cragg | 623/1 |
| 5,683,453 | 11/1997 | Palmaz | 623/1 |
| 5,693,085 | 12/1997 | Buirge et al. | 623/1 |
| 5,700,285 | 12/1997 | Myers et al. | 623/1 |
| 5,713,917 | 2/1998 | Leonhardt et al. | 606/194 |
| 5,723,004 | 3/1998 | Dereume et al. | 623/1 |
| 5,735,892 | 4/1998 | Myers et al. | 623/1 |
| 5,741,324 | 4/1998 | Glastra | 623/1 |
| 5,749,880 | 5/1998 | Banas et al. | 606/198 |

STENT-GRAFT ASSEMBLY WITH DUAL CONFIGURATION GRAFT COMPONENT AND METHOD OF MANUFACTURE

FIELD OF THE INVENTION

The present invention relates generally to endoluminal prostheses used in the treatment of stenotic or diseased lumens, and methods of making such prostheses. More particularly, the invention relates to a covered endoluminal prosthesis assembly and methods of making the assembly.

BACKGROUND OF THE INVENTION

Numerous expandable endoluminal prostheses are known in the art which are adapted for temporary or permanent implantation within a body lumen for maintaining the patency of the lumen. Examples of lumens, both native and artificially made, in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes.

Each of the various types of endoluminal prostheses known in the art provides a uniquely beneficial structure to modify the mechanics of the targeted luminal wall. Many devices known in the art are also designed to provide a desirable healing surface for the vessel wall following treatment. Others are designed to achieve further objectives such as, for example, excluding an aneurysm.

For example, devices generally referred to as stents provide radial support to the lumen. Stents may be mechanically expandable, balloon expandable or self-expanding. Stent-grafts are typically stents with a covering, lining, coating, or some combination of the foregoing. Various grafts, stents, and combination stent-graft prostheses have been previously disclosed for implantation within body lumens.

A common procedure to enlarge a stenotic or diseased blood vessel is known as percutaneous transluminal angioplasty, or PTA. PTA employs an angioplasty balloon catheter which is inserted at a site remote from the site of treatment, tracked to the stenosis, and placed across the lesion. The balloon is then inflated to dilate the artery. In order to prolong the positive effects of PTA and to provide long-term radial support to the treated vessel, a stent or stent-graft may be implanted in conjunction with the procedure. Under this procedure, the stent may be mounted on the balloon, collapsed to an insertion diameter, delivered to the treatment site within the affected lumen, and deployed to its desired diameter for treatment. Because the procedure requires insertion of the stent at a site remote from the site of treatment, the device must be guided through the potentially tortuous conduit of the body lumen to the treatment site. Therefore, the stent must be capable of being reduced to a small insertion diameter and must be flexible.

During an angioplasty procedure, atheromatous plaques within the vessel can undergo fissuring, thereby creating a thrombogenic environment in the lumen. Excessive scarring may also occur following the procedure, potentially resulting in restenosis or reocclusion of the treated lumen. Attempts to address these problems include providing a suitable surface within the lumen for more controlled healing to occur in addition to the support provided by a stent. These attempts include providing a lining or covering in conjunction with an implanted stent. A stent with such a lining or covering is known in the art as a stent-graft.

Specific examples of stents include U.S. Pat. Nos. 5,292,331 and 5,674,278, both issued to Boneau, which are herein incorporated by reference. The stent of Boneau comprises a, or a series of sinusoidally shaped ring-like. Such a stent exhibits excellent radial strength and flexibility.

Other types of stents are disclosed in U.S. Pat. Nos. 4,733,665, 4,776,337, 4,739,762 and 5,102,417 all issued to Palmaz, U.S. Pat. No. 5,195,984 issued to Schatz, U.S. Pat. No. 5,421,955 issued to Lau et al., or U.S. Pat. No. 5,449,373 issued to Pinchasik et al. Such stents include examples of stents created by removing material, such as by cutting or forming, from a thin-walled tube or sheet of material.

All of the foregoing examples of stents may be used alone or in conjunction with a graft. The graft component, or membrane, of a stent-graft may prevent excessive tissue prolapse or protrusion of tissue growth through the interstices of the stent while allowing limited tissue in-growth to occur to enhance the implantation. The surface of the graft material at the same time may minimize thrombosis, prevent scarring from occluding the lumen, prevent embolic events and minimize the contact between the fissured plaque and the hematological elements in the bloodstream.

A combination stent-graft may serve other objectives, such as delivering therapeutic agents via the assembly, excluding aneurysms or other malformations, occluding a side branch of a lumen without sacrificing perforator branches, conferring radiopacity on the device, and others. Various designs to achieve these objectives include stents partially or completely coated or covered with materials, some of which are impregnated with therapeutic agents, radiopaque elements, or other features designed to achieve the particular objectives of the device.

Various methods of manufacturing graft devices alone have been disclosed in the art. One such method for manufacturing a graft is disclosed in U.S. Pat. No. 5,641,373, issued to Shannon et al. The disclosed method comprises reinforcing an extruded fluoropolymer tube with a second fluoropolymer tube. The second tube is prepared by winding fluoropolymer tape around the exterior of a mandrel and heating it to form a tube. The graft may then be mounted on an anchoring mechanism such as a stent or other fixation device.

Another example of a graft is disclosed in U.S. Pat. No. 4,731,073, issued to Robinson. The graft disclosed therein comprises multiple layers of segmented polyether-polyurethane which form multiple zones having varying porosities.

U.S. Pat. No. 5,628,786, issued to Banas, discloses a polytetrafluoroethylene (PTFE) graft which has a reinforcing structure integrally bound to the graft. The reinforcing structure may be in the form of a rib which is sintered or otherwise integrally bound to the graft.

U.S. Pat. No. 5,207,960, issued to Moret de Rocheprise, discloses a process for the manufacture of a thin-walled tube of fluorinated resin tape. The method includes winding the tape around a mandrel and sintering the tape. While still on the mandrel, the tube is rolled to elongate the tube, to reduce the thickness of the tube, and to facilitate removal of the tube from the mandrel. The patent discloses that the tubes obtained can be used particularly as sheaths for the lining of metal tubes.

There are also numerous examples of combination stent-grafts disclosed in the art. U.S. Pat. No. 5,667,523 issued to Bynon et al. discloses a stent-graft comprising two stents and graft material positioned between the two stents.

U.S. Pat. No. 5,653,747 issued to Dereume discloses a stent to which a graft is attached. The graft component is produced by extruding polymer in solution into fibers from a spinnerette onto a rotating mandrel. A stent may be placed over the fibers while on the mandrel and then an additional layer of fibers spun onto the stent. The layer or layers of fibers may be bonded to the stent and/or one another by heat or by adhesives.

PCT Application WO 95/05132 discloses a stent around which a thin film of PTFE has been wrapped circumferentially one time and overlapped upon itself to form a seam. The stent may be alternatively or additionally placed to cover the interior of the stent. Fluorinated ethylene propylene is used as an adhesive to affix the graft to the stent.

An example of a stent and tubular graft is disclosed in U.S. Pat. No. 5,522,882 issued to Gaterud, et al. Gaterud discloses an expandable stent mounted on a balloon and a graft mounted over the stent.

U.S. Pat. No. 5,123,917 issued to Lee discusses a flexible and expandable inner tube upon which separate ring-like scaffold members are mounted, and a flexible and expandable outer tube enclosing the inner tube and scaffold members. The rings may be secured to the inner liner with an adhesive layer. Alternatively, the liners may be adhered to each other with the rings trapped between the layers. Lee discloses that the luminal surface of the device may be coated with various pharmacological agents.

Similarly, U.S. Pat. Nos. 5,282,823 and 5,443,496, both issued to Schwartz, et al. disclose a stent with a polymeric film extending between the stent elements, and strain relief means in the form of cuts in the film to allow the stent to fully expand and conform to the interior of the lumen. The thin polymeric film is applied to the stent while in solution and dried. Once dried, cuts are made in the film to provide strain relief means.

Another assembly includes a stent embedded in a plastic sleeve or stitched or glued to a nylon sleeve, as in U.S. Pat. No. 5,507,771, issued to Gianturco. Other references disclosing devices in which the graft is stitched to the stent include European Patent Application EP 0 686 379 A2, which teaches a perforate tubular frame having a fabric liner stitched to the frame, and World Intellectual Property Organization Application Number WO 96/21404 which indicates that the graft be stitched to the stent, and possibly to loops or eyelets which are part of the stent structure.

U.S. Pat. No. 5,637,113 issued to Tartaglia teaches a stent with a sheet of polymeric film wrapped around the exterior. Tartaglia teaches that the film is attached to the stent at one end by an adhesive, by a hook and notch arrangement, or by dry heat sealing. The polymer can also be attached to the stent by wrapping the film circumferentially around the stent and attaching the polymer film to itself to form a sleeve around the stent by heating and melting the film to itself, adhesive bonding, solvent bonding, or by mechanical fastening, such as by a clip. The film may be loaded or coated with a therapeutic agent.

U.S. Pat. No. 5,628,788, issued to Pinchuk, discloses a process of melt-attaching a graft to a stent by disposing a layer of material between the stent and graft which has a lower melting point than the graft, and heating the assembly to the melting point of the low-melting point material. Pinchuk also teaches adhering a textile graft to a stent by coating a stent with vulcanizing silicone rubber adhesive and curing the adhesive. Pinchuk discloses a similar stent-graft assembly in European Patent Application EP 0 689 805 A2 and teaches that the graft member can be bonded to the stent member thermally or by the use of adhesive agents.

Similarly, World Intellectual Property Organization Application No. WO 95/05132 discloses a stent with an inner and/or an outer liner wrapped around the stent to form a seam, with the liner(s) affixed using an adhesive or melt-attached using a layer of a material with a lower melting point.

U.S. Pat. No. 5,645,559, issued to Hachtman, et al., discloses a multiple layer stent-graft assembly comprising a first layer defining a hollow tubular construction, a second layer having a self-expanding braided mesh construction and a layer of polymeric material disposed between the first and second layers. The polymeric material may be adhered by two-sided adhesive tape. The self-expanding braided mesh, the tubular material, or both may be larger in diameter in the distal regions than in the medial region.

U.S. Pat. No. 5,534,287, issued to Lukic, discloses methods which result in a covered stent, the covering adhered via a lifting medium.

U.S. Pat. No. 5,674,241, issued to Bley, et al. teaches that a hydrophilic polymer layer may be laminated, embedded, coated, extruded, incorporated, or molded around an expandable mesh stent while the stent is in its collapsed condition, and the stent and graft permitted to expand upon hydration.

European Patent Application No. EP 0 775 472 A2 discloses a PTFE-covered stent. The stent can be covered by diagonally winding an expanded PTFE tape under tension around an at least partially expanded stent.

Challenges arising in the art which none of the prior art adequately addresses include achieving an optimal stent-graft design for delivery and deployment of the device. Other challenges which are not adequately addressed by the prior art include minimizing, if not eliminating, migration of the stent, graft or stent-graft; and minimizing thrombogenic potential, vessel reocclusion and tissue prolapse following deployment. Shortcomings associated with the prior art include: assemblies with undesirably large crossing profiles; assemblies with insufficient flexibility; inadequate adhering of coatings and coverings to stents; failure to shield the injured vascular surface; failure to prevent tissue ingrowth from occluding the lumen; failure to minimize the embolization of particles loosely adherent to the vessel wall (especially during device placement and deployment); and increased thrombogenic potential arising from flaps formed in the graft material.

SUMMARY OF THE INVENTION

The present invention and its varied embodiments address several problems associated with the prior art. It is a first objective of this invention to provide an improved stent-graft assembly for the repair and support of a body lumen. It is a second objective of this invention to provide an improved stent-graft assembly with ample radial strength and minimal thrombogenic potential without appreciably increasing the profile of the device over that of the stent alone.

It is a further objective of this invention to provide a stent-graft assembly in which the graft component is both sufficiently secured to the stent, yet sufficiently free during deployment of the device to achieve a desired configuration of the graft component with respect to the stent. Further, the stent and graft have a delivery configuration and an alternative, post-deployment configuration.

An additional objective of this invention is to balance the need for some tissue in-growth against the need to minimize thrombogenic potential and excessive cell growth through the interstices of the stent. This objective is also achieved by providing a stent-graft assembly which shields the injured vascular surface throughout, controls excessive tissue in-growth through the stent, and minimizes the embolization of particles loosely adherent to the vessel wall especially during placement and deployment of the device. The device can also be used to control the luminal protrusion of dissection planes created during PTA or spontaneous fissuring.

A stent-graft assembly according to the present invention first comprises a generally cylindrical stent. Further, the stent-graft includes a graft member or covering disposed about its outer diameter which comprises a first length before deployment and a second length after deployment. Further, the graft comprises a delivery configuration and a treatment configuration. Before deployment, the graft member has a greater length than the stent, and the ends of the graft are inverted to line the inner diameter of the stent, generally at the ends of the stent. The graft member is radially distensible. Upon expansion of the device, the graft component foreshortens such that it unfolds, pulls away from the inner diameter of the stent, and does not cover the ends of the stent once deployment is complete. A suture or sutures attaching the graft to the stent ensures that the graft remains well-centered over the stent during deployment.

The method of manufacturing the assembly according to a first embodiment of the present invention comprises helically wrapping a polymeric tape around a mandrel. The tape is wrapped at a particular angle to the perpendicular axis of the mandrel in order to achieve the desired distensibility of the membrane. The method further comprises sintering the tape to itself over the mandrel under particular parameters to produce a thin tube with desired radial distensibility; removing the thin tube from the mandrel; covering the stent with the thin tube; suturing the graft to the stent; and invertedly folding the ends of the graft over the ends of the stent.

DETAILED DESCRIPTION OF THE PREFERRED EMBODIMENTS

Figure 1:
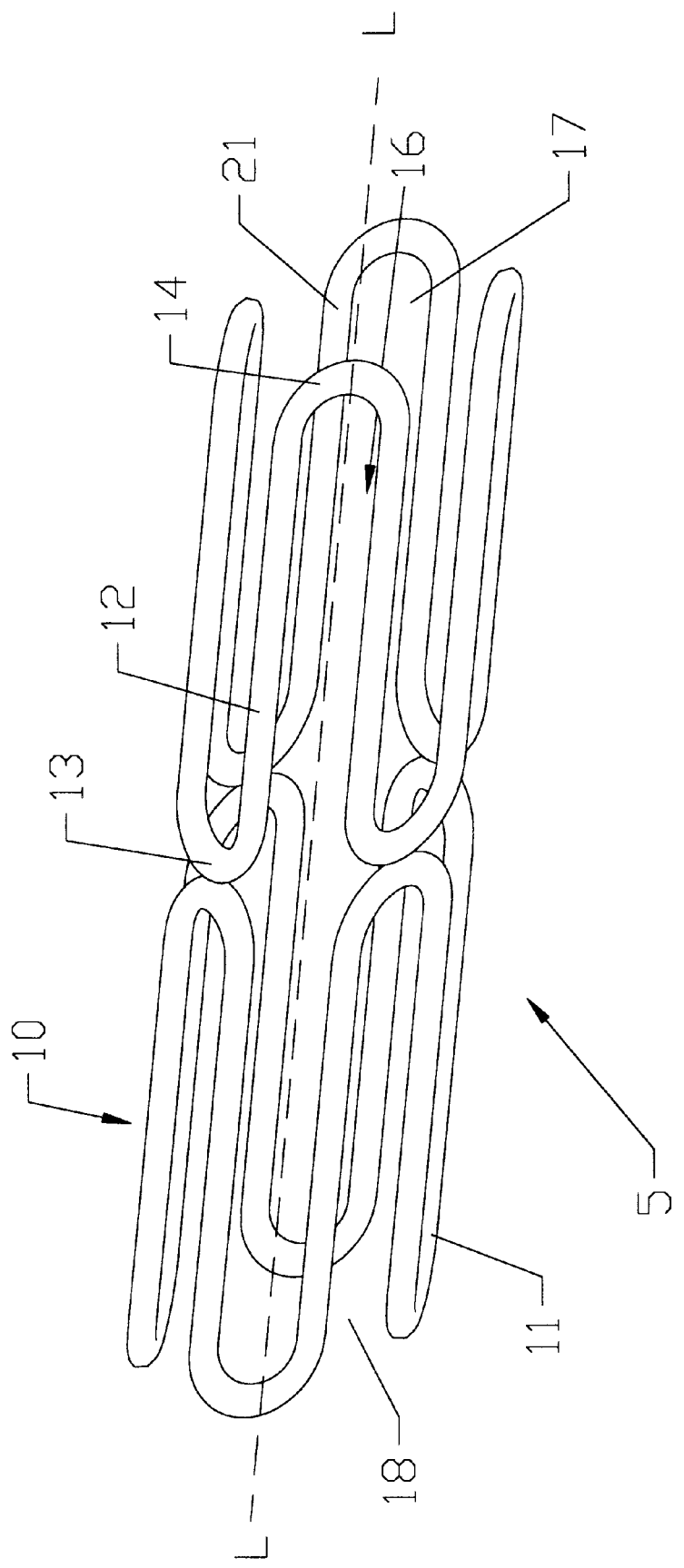
FIG. 1 illustrates a perspective view of a suitable stent for use in the present invention.
Figure 2:
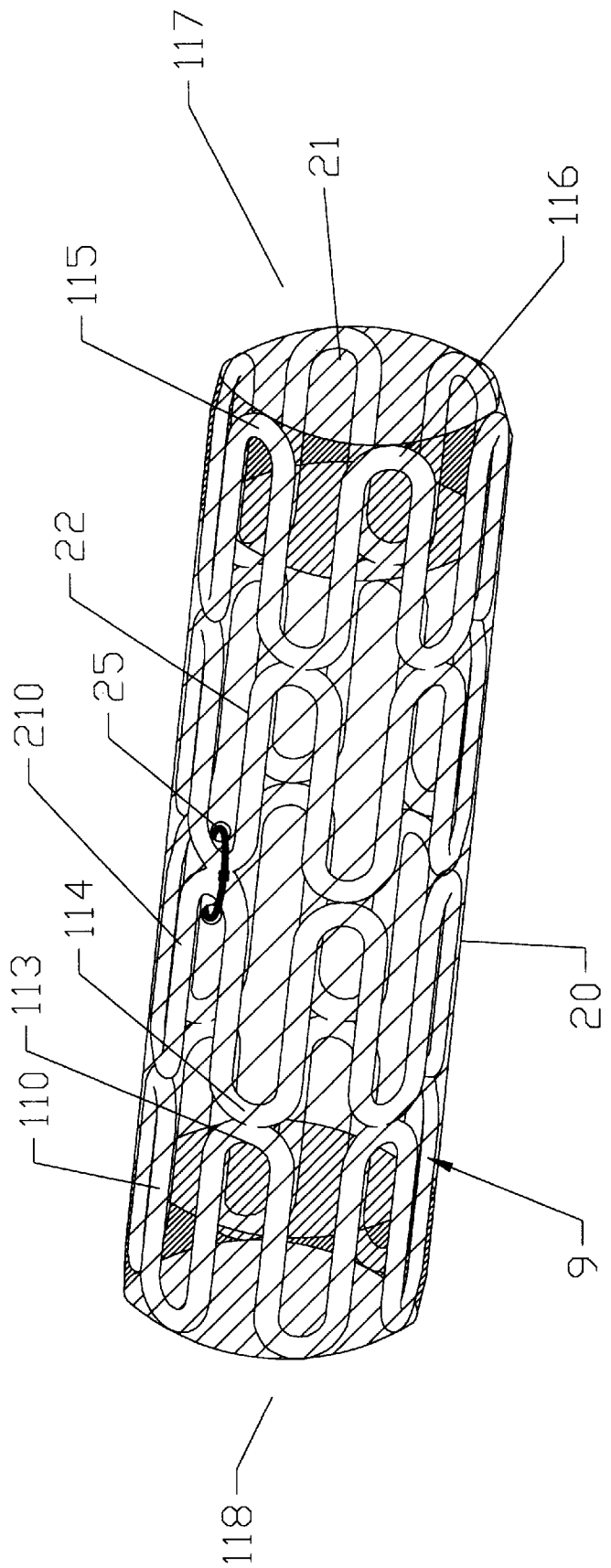
FIG. 2 illustrates a perspective view of an embodiment of the stent-graft assembly according to the present invention prior to deployment.

The thin-walled stent-graft assembly according to the present invention is shown in FIG. 2. One recommended stent for use as the stent member according to the present invention is shown as stent 5 in FIG. 1. Other stents, including but not limited to those disclosed in U.S. Pat. No. 4,733,417 issued to Palmaz, U.S. Pat. No. 5,195,984 issued to Schatz, or U.S. Pat. No. 5,514,154 issued to Lau may also be suitable for use in the stent graft assembly.

Stent 5 is shown in FIG. 1 to include a series of connected, individual sinusoidal-shaped stent elements 10. Stent 5 can comprise any number of stent elements 10, including simply one such element. Each individual element is similar in design and construction to the endovascular support device disclosed in U.S. Pat. No. 5,292,331 issued to Boneau, the disclosure of which is incorporated herein. For the purpose of further illustration, however, the series of adjacent rings or circumferential wires form support members, such as is shown for the purpose of illustration at support member 11. Each ring is formed to include a sinusoidal or serpentine shape which includes a plurality of peaks and substantially straight support members or struts extending longitudinally between adjacent peaks. An example is such as is shown at strut 12 which extends between peaks 13 and 14. Each ring is further connected to an adjacent ring in at least one location where the peaks of their serpentine shape meet, resulting in an interconnected series of stent elements which forms the generally cylindrical stent 5. Stent 5 further forms a prosthesis passageway 16 extending through the plurality of adjacent, serpentine-shaped rings along longitudinal axis L, and between proximal prosthesis port 17 and distal prosthesis port 18.

Further to the interconnected series of stent elements and their respective wire-like support members which form cylindrical body 15 as shown in FIG. 1, spaces remain along cylindrical body 15 between adjacent peaks of each shaped ring and also between adjacent rings, particularly where the individual peaks of adjacent rings extend away from each other relative to longitudinal axis L.

Turning now to FIG. 2, a stent-graft assembly according to one embodiment of the present invention comprises a stent 9 comprising a plurality of stent elements such as stent element 110 comprising a plurality of peaks such as indicated at 113, 114, 115 and 116. In the embodiment depicted in FIG. 2, peaks of successive stent elements such as stent elements 110 and 210 meet one another. For example, peak 113 of stent element 110 is proximate peak 114 of stent element 210. Further, one or more, but preferably each peak of the stent elements at the ends of the device adjoin the contiguous peak of the adjacent stent element. For example, peak 113 adjoins peak 114. Consequently, the rings or stent elements on each end of the device of FIG. 2 are connected to the remainder of the stent at each peak, such as by fusing, welding, soldering or other suitable method. If a stent which is cut from a tube is utilized in preparing the assembly, such connections are left intact. Such connections prevent graft 20 or other similar graft from lapsing between the peaks during and after deployment of the device, and increase the radial strength of the device.

The assembly of FIG. 2 further comprises graft 20 which in this embodiment covers the stent to define a relatively continuous vascular surface 22, but which in alternate embodiments may line the inner diameter of the stent to form a luminal surface, or may define both a vascular and luminal surface. The graft is preferably between 0.001 and 0.003 inch in thickness, is radially distensible, and foreshortens over a range of between 20 and 50 per cent from its primary or initial length. Suitable material for the graft may be synthetic and is preferably expanded polytetrafluoroethylene (ePTFE), but may include and is not limited to polyesters, polyurethane and silicone.

Graft 20 is folded invertedly to define a luminal surface 21 adjacent the proximal prosthesis port 117 and adjacent the distal prosthesis port 118. Suture 25 ensures that the graft remains well-centered over the stent during deployment of the device.

Figure 3:
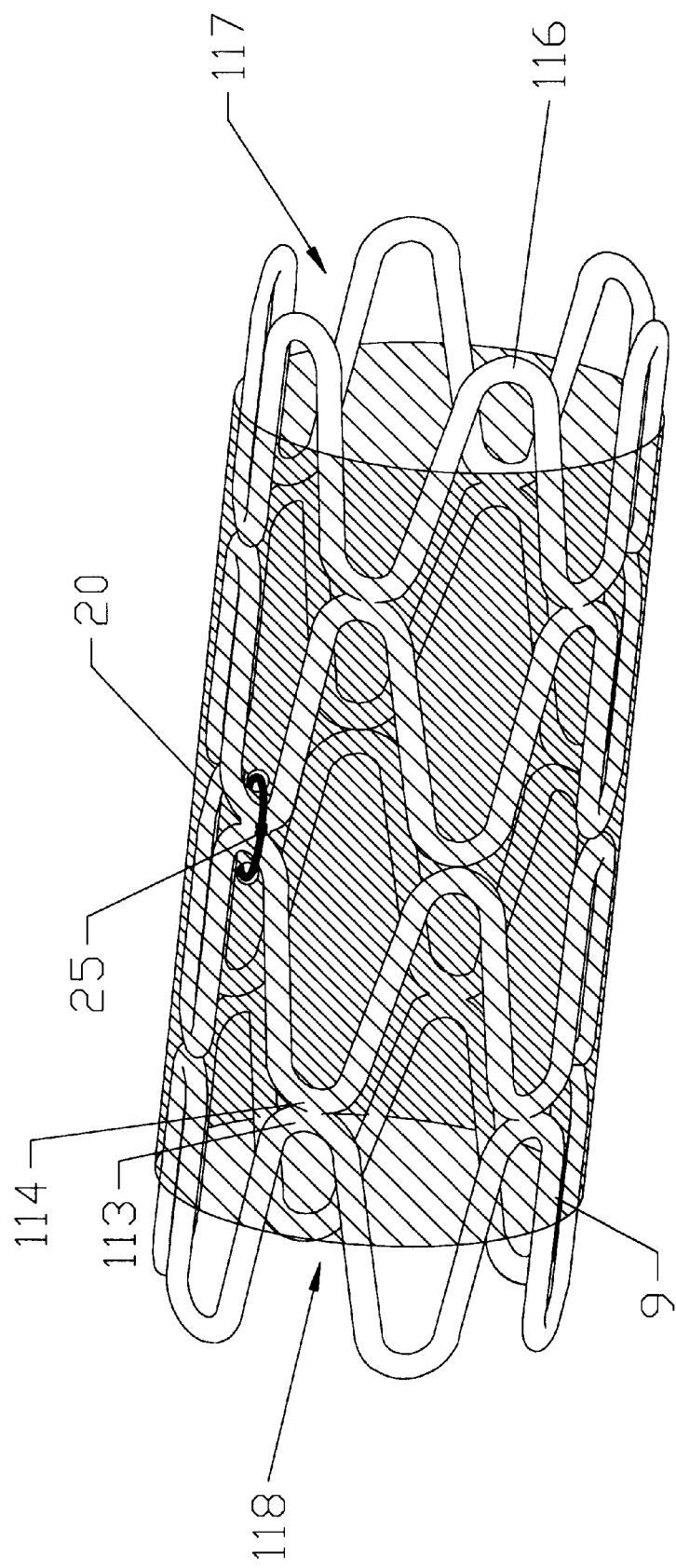
FIG. 3 illustrates a perspective view of an embodiment of the stent-graft assembly according to the present invention following deployment.

FIG. 3 illustrates the stent graft assembly of FIG. 2 following deployment. Graft 20 is no longer folded to define a luminal surface, but rather has foreshortened to unfold and to come away from the inner diameter of the stent. Peaks (such as peak 116) which define proximal prosthesis port 117 and distal prosthesis port 118 may now be exposed. Preferably, the graft remains over essentially the entire length of the stent, but may recede as far as to expose the entire stent elements at the ends of the stent.

Figure 4:
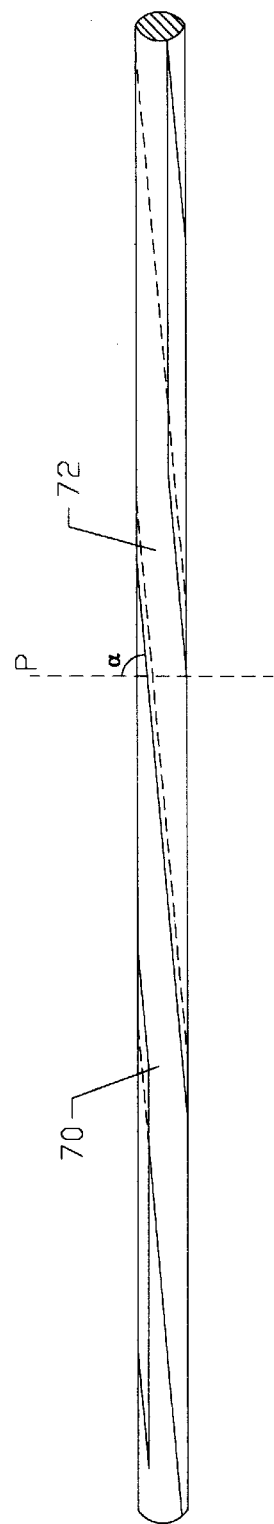
FIGS. 4–7 illustrate a stent-graft assembly as it appears following illustrative, successive steps of preparation of the assembly.
Figure 5:
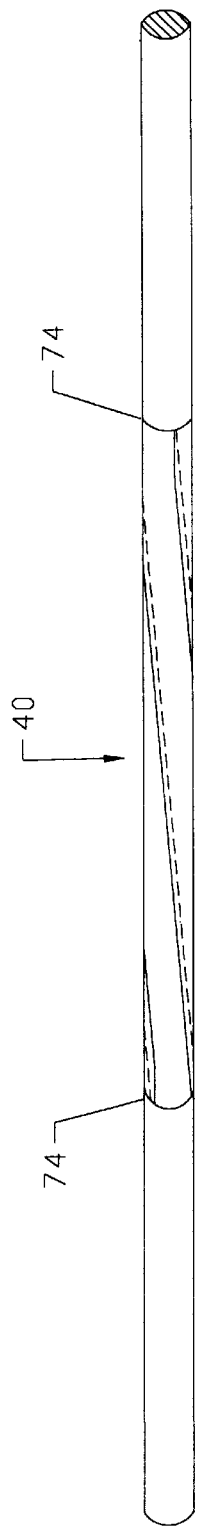

A portion of the method of preparation of the thin-walled graft component is illustrated in FIGS. 4 and 5. Successive helical windings 70 of the polymeric tape 72 overlap to a relatively large extent given the steep angle of orientation of the tape to the axis perpendicular to the mandrel. The finished graft component is greatly distensible as a result of the angle α of the tape to the axis P, which is perpendicular to the longitudinal axis of the mandrel. In general, the greater the angle α, the greater the radial distensibility. The degree of distensibility is also somewhat affected by the sintering process, but to a lesser degree than as a result of the wrap angle. In this embodiment angle α may be between 70 and 87 degrees, and is preferably between 80 and 85 degrees. The tape is wound beginning from one end of the mandrel progressively to the other end of the mandrel. The ends of the wrapped tape tube may be clamped to the mandrel in order to prevent foreshortening of the tube during the sintering process, which follows.

The wrapped mandrel is then subject to a sufficient temperature for a sufficient time to sinter the overlapping layers together. For example, a ePTFE-wrapped mandrel is subject to a temperature between 360 and 370 degrees C for between 20 and 60 minutes to sinter the overlapping portions together. Pressure may be utilized in conjunction with sintering to improve the adherence of the tape windings to one another. The ends 74 of the tube may then be trimmed to form a tube of desired length.

Graft 40 is then removed from the mandrel. If, because the tube constricts to some degree during sintering, difficulty is encountered in removing the tube from the mandrel, several methods to facilitate removing the tube may be used. Compressed air may be discharged at one end of the tube between the tube and the mandrel, or a flat tool may be used to loosen any temporary adhesion between the mandrel and the tube. Alternatively, a collapsible mandrel or a bar of reducible diameter may be used. Also, a lubricant such as silicone, can be introduced to facilitate removal of the tube from the mandrel.

Figure 6:
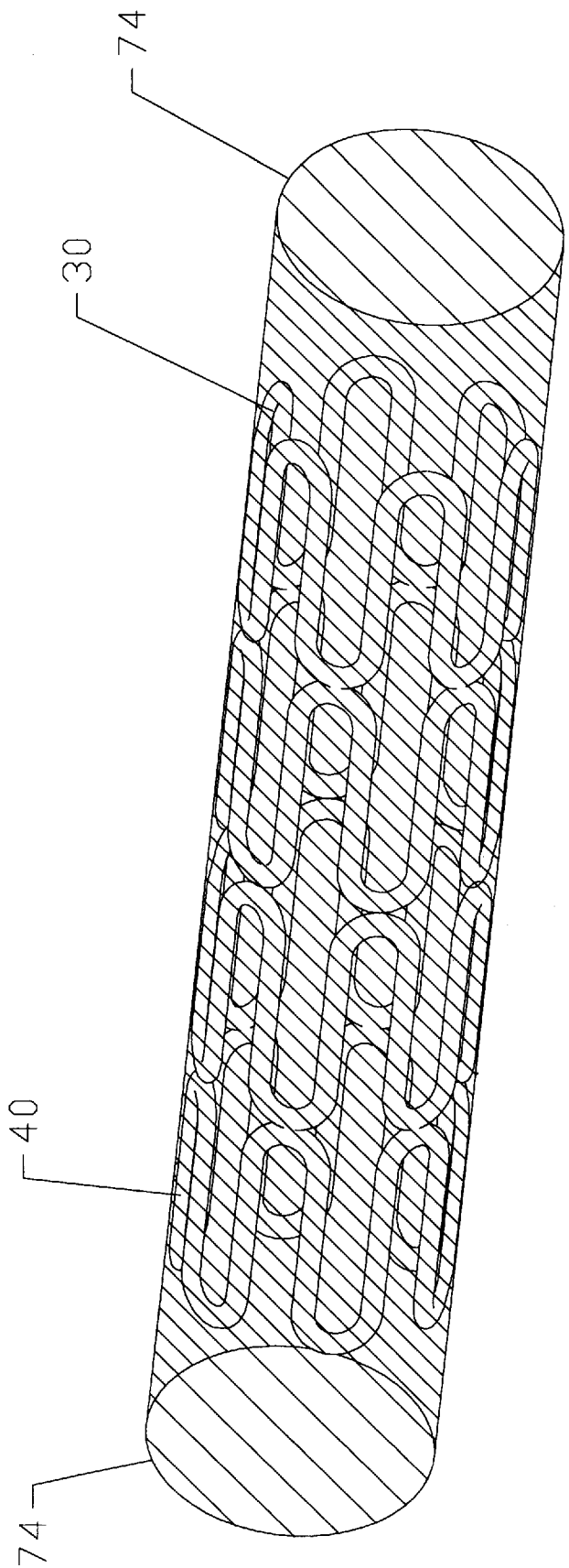
Figure 7:
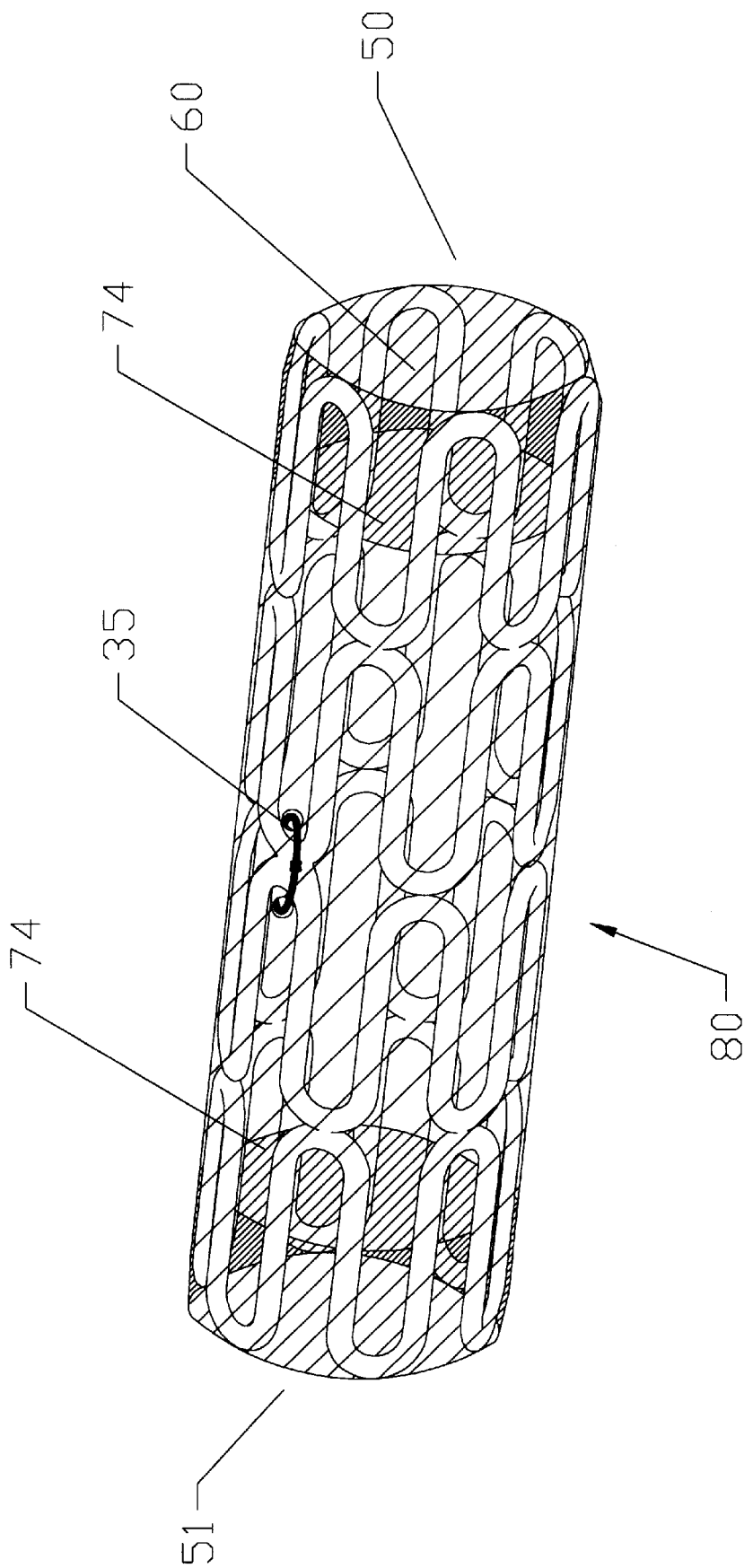

Newly prepared graft 40 is then loaded over stent 30, as depicted in FIG. 6. Graft 40 is centered over and sutured to the stent, preferably utilizing a polypropylene suture material. The ends of the suture material and/or the knot formed in suture 35 may then be melted utilizing a point contact device. Ends 74 of graft 40 are then folded invertedly into the proximal prosthesis port 50 and distal prosthesis port 51, to define luminal surface 60 adjacent proximal prosthesis port 50 and a luminal surface (not pictured) adjacent distal prosthesis port 51. The finished stent-graft assembly 80 according to one embodiment of the invention is depicted in FIG. 7. Specific examples of manufacturing the assembly follow.

EXAMPLE 1

For the purpose of further illustration, an exemplary method for preparing a stent-graft assembly is described as follows. A thin tape of ePTFE, manufactured by Baxter, Inc., of approximately 0.0004 inch in thickness, was wound around a 0.047 inch mandrel under slight tension at approximately an 85 degree angle to the perpendicular axis of the mandrel. The wrapped mandrel was sintered at 367 degrees Celsius for 25 minutes. After cooling, the tube was removed from the mandrel and trimmed to form a 20.5 mm long tube.

A GFX® stent, which is manufactured by Arterial Vascular Engineering, Inc., in Santa Rosa, Calif., was provided in a 18 mm length. Each peak of the stent elements at the ends of the stent which abutted an adjacent peak were welded to the abutting peak.

The thin ePTFE tube was removed from the mandrel and placed, well-centered, over the stent. The graft was then attached to the stent with two polypropylene sutures. The ends of the suture material and knot formed by the ends were melted using a heated point contact device at 360 degrees F. The graft material, which extends beyond the ends of the stent, was then folded invertedly to touch the inner diameter of the stent at the ends.

EXAMPLE 2

A further example of a method of preparation of a stent-graft assembly according to the invention is as follows. ePTFE tape manufactured by Baxter, Inc. was circumferentially wrapped around a 0.058 inch mandrel, under slight tension at approximately an 85 degree angle to the perpendicular axis of the mandrel. The tape-wrapped mandrel was then sintered at 367 degrees Celsius for 25 minutes. The sintered tape and mandrel were allowed to cool, and the ends of the graft were trimmed, resulting in a 23 mm long graft.

A 21 mm long GFXtra stent manufactured by Arterial Vascular Engineering, Inc. was provided. Additional welds at the end stent elements between abutting peaks were made. The graft was loaded over the stent. The graft, well-centered, was sutured to the stent using polypropylene suture material. The ends of the suture material and knot formed by the ends were melted using a heat point contact device at 360 degrees F. The ends of the graft were then folded under, into the inside of the stent, and against the interior surface of the stent.

A stent-graft assembly having a graft having a dual configuration and method of manufacturing the same have been disclosed. Although the present invention has been described in accordance with the embodiments shown, one of ordinary skill in the art will readily recognize that there could be variations to the embodiments and those variations would be within the spirit and scope of the present invention.

A wide variety of suitable materials used for stents and grafts may be interchanged without diverging from the methods or structures of the invention claimed. For example, the type of stent utilized could be varied greatly. The embodiments disclosed herein focus on a stent comprising independent support members, but an alternate stent which is comprised of a slotted tube or of a rolled film or sheet configuration may also be used. Further, suitable stents include stents made of nitinol or other shape memory alloy. In order to confer or enhance radiopacity on an alternative stent, various methods may be utilized. For example, a radiopaque metal marker such as gold, tantalum, platinum, iridium or any alloy thereof may be attached to the graft material.

Further, the instant invention can also be used for indications other than repairing and/or providing radial support to a body lumen. Other examples include aneurysm isolation and vessel occlusion. The foregoing embodiments and examples are illustrative and are in no way intended to limit the scope of the claims set forth herein.

What is claimed is:

1. A stent-graft assembly comprising:
   a generally cylindrical, radially expandable stent having a length and first and second ends;
   a generally tubular, radially expandable graft member having first and second ends, a first length when in a first configuration and a second length when in a second configuration, said first length being greater than said second length and, said graft member covering said stent;

wherein said first length of said graft member is greater than the length of said stent when said graft member is in said first configuration;

wherein the ends of the graft member are folded over the ends of the stent when the graft member is in said first configuration, and the ends of said graft member are not folded over the ends of the stent when the graft member is in said second configuration; and wherein said graft member is in said first configuration prior to expansion of the stent, and said second configuration following expansion of said stent.

2. The stent-graft assembly of claim 1 wherein the length of the graft member when in the second configuration is between 20% and 40% less than the length of the graft when the graft is in the first configuration.

* * * * *